(12) United States Patent
Kathrani et al.

(10) Patent No.: US 7,585,290 B2
(45) Date of Patent: Sep. 8, 2009

(54) MEDICAL DEVICE FOR PROVIDING ACCESS

(75) Inventors: Biten K. Kathrani, Mumbai (IN); Tehemton E. Udwadia, Mumbai (IN); Mangesh Pantankar, Nashik (IN)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 805 days.

(21) Appl. No.: 10/761,159

(22) Filed: Jan. 20, 2004

(65) Prior Publication Data
US 2005/0159711 A1    Jul. 21, 2005

(51) Int. Cl.
*A61M 5/00* (2006.01)
(52) U.S. Cl. .......................................... 604/264; 604/26
(58) Field of Classification Search .................. 604/264, 604/164.09, 26, 164.11, 158, 256, 23–27, 604/115, 164.01, 164.07, 164.08, 171–172; 606/172
See application file for complete search history.

(56) References Cited

U.S. PATENT DOCUMENTS

| | | | | |
|---|---|---|---|---|
| 3,896,810 A * | 7/1975 | Akiyama | ...................... | 604/117 |
| 4,014,333 A * | 3/1977 | McIntyre | ...................... | 604/43 |
| 4,610,242 A * | 9/1986 | Santangelo et al. | .......... | 600/114 |
| 4,803,999 A * | 2/1989 | Liegner | ...................... | 600/576 |
| 5,112,308 A * | 5/1992 | Olsen et al. | ............. | 604/164.09 |
| 5,186,714 A | 2/1993 | Boudreault et al. | | |
| 5,312,363 A * | 5/1994 | Ryan et al. | ............. | 604/167.04 |
| 5,336,172 A | 8/1994 | Bales et al. | | |
| 5,336,220 A | 8/1994 | Ryan et al. | | |
| 5,389,077 A * | 2/1995 | Melinyshyn et al. | ........ | 604/117 |
| 5,391,156 A * | 2/1995 | Hildwein et al. | ............ | 604/174 |
| 5,439,457 A | 8/1995 | Yoon | | |
| 5,456,684 A | 10/1995 | Schmidt et al. | | |
| 5,505,710 A * | 4/1996 | Dorsey, III | ................... | 604/158 |
| 5,593,402 A | 1/1997 | Patrick et al. | | |
| 5,613,954 A | 3/1997 | Nelson et al. | | |
| 5,733,252 A | 3/1998 | Yoon | | |
| 5,766,169 A | 6/1998 | Fritzsch et al. | | |
| 5,792,112 A | 8/1998 | Hart et al. | | |
| 5,797,882 A * | 8/1998 | Purdy et al. | ............. | 604/164.09 |
| 5,797,939 A | 8/1998 | Yoon | | |
| 5,800,389 A * | 9/1998 | Burney et al. | .......... | 604/164.01 |

(Continued)

FOREIGN PATENT DOCUMENTS

CA    2213540    2/1999

OTHER PUBLICATIONS

EPO Search Report dated Mar. 29, 2005 for corresponding patent application, European Patent Application No. EP 05 25 0242.

*Primary Examiner*—Nicholas D Lucchesi
*Assistant Examiner*—Theodore J Stigell

(57) ABSTRACT

The invention provides, in one embodiment, a multifunctional, multi-piece medical device and related method for providing access to an internal body cavity, such as for use with a vacuum lift shell. The device can include a cannula and a cannula extension. The device provides a conduit between the external environment and operative field inside the patient's body during medical procedures, including diagnostic, therapeutic and surgical procedures. The invention allows entry and exit of air or gas to help create and maintain the operative field. The invention can be used to provide an open and unobstructed working path, and allows the operative space to be maintained at ambient conditions of pressure and temperature.

15 Claims, 16 Drawing Sheets

U.S. PATENT DOCUMENTS

| | | | |
|---|---|---|---|
| 5,823,947 A | 10/1998 | Yoon et al. | |
| 5,827,323 A | 10/1998 | Klieman et al. | |
| 5,865,802 A | 2/1999 | Yoon et al. | |
| 5,893,368 A | 4/1999 | Sugerman | |
| 5,913,848 A * | 6/1999 | Luther et al. | 604/524 |
| 5,938,626 A | 8/1999 | Sugerman | |
| 5,984,939 A | 11/1999 | Yoon | |
| 6,042,539 A | 3/2000 | Harper et al. | |
| 6,099,550 A | 8/2000 | Yoon | |
| 6,117,152 A | 9/2000 | Huitema | |
| 6,120,437 A | 9/2000 | Yoon et al. | |
| 6,296,624 B1 * | 10/2001 | Gerber et al. | 604/164.11 |
| 6,432,118 B1 | 8/2002 | Messerly | |
| 6,436,117 B1 | 8/2002 | Waller et al. | |
| 6,478,775 B1 * | 11/2002 | Galt et al. | 604/158 |
| 6,554,793 B1 | 4/2003 | Pauker et al. | |
| 6,554,829 B2 | 4/2003 | Schulze et al. | |
| 6,582,441 B1 | 6/2003 | He et al. | |
| 6,916,310 B2 * | 7/2005 | Sommerich | 604/175 |
| 2002/0099375 A1 | 7/2002 | Hess et al. | |
| 2002/0143355 A1 | 10/2002 | Messerly | |
| 2002/0177849 A1 | 11/2002 | Schulze et al. | |
| 2002/0183775 A1 | 12/2002 | Tsonton et al. | |
| 2002/0188294 A1 | 12/2002 | Couture et al. | |
| 2002/0198525 A1 | 12/2002 | Schulze et al. | |
| 2002/0198554 A1 | 12/2002 | Whitman et al. | |
| 2003/0004528 A1 | 1/2003 | Ishikawa | |
| 2003/0004529 A1 | 1/2003 | Tsonton et al. | |
| 2003/0014010 A1 | 1/2003 | Carpenter et al. | |
| 2003/0023257 A1 | 1/2003 | Ishikawa | |
| 2003/0060770 A1 | 3/2003 | Wing et al. | |
| 2003/0065358 A1 | 4/2003 | Frecker et al. | |
| 2003/0083628 A1 | 5/2003 | Blanco | |
| 2003/0105485 A1 | 6/2003 | Balceta et al. | |

* cited by examiner

FIG. 3 FIG. 5 FIG. 6
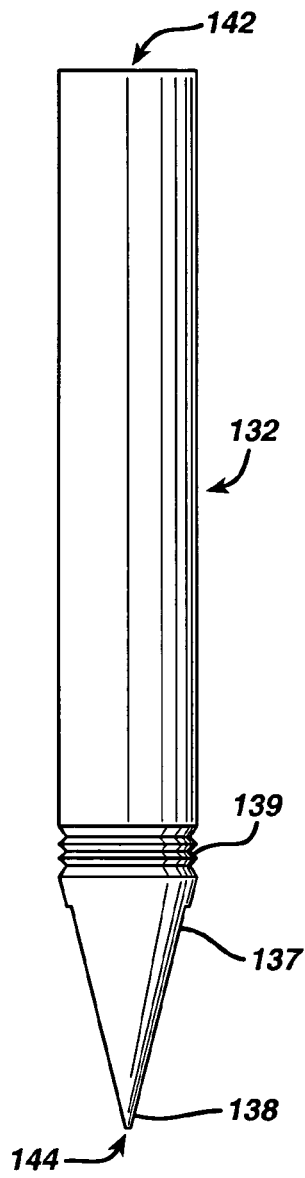
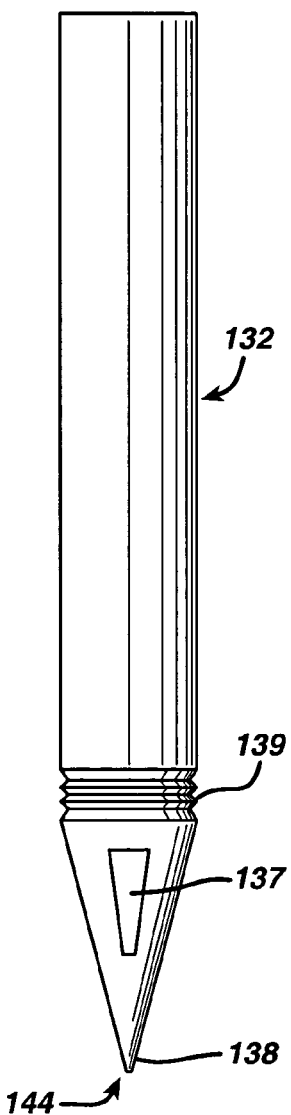
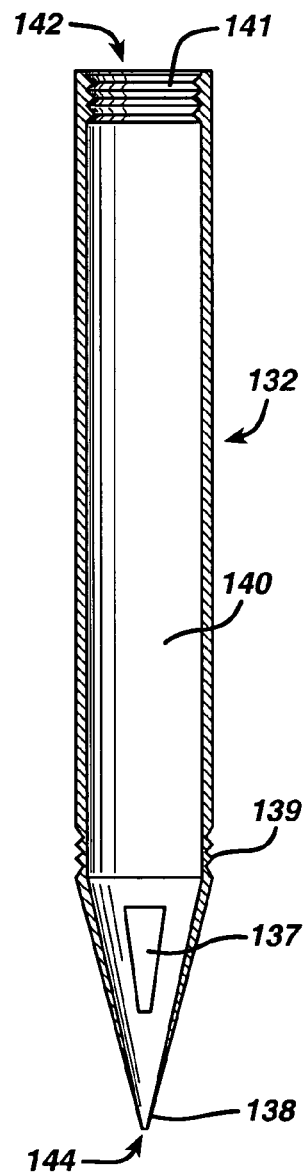
FIG. 4
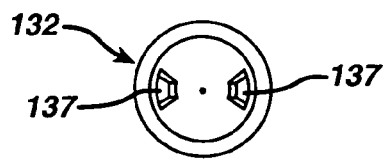

FIG. 11     FIG. 13
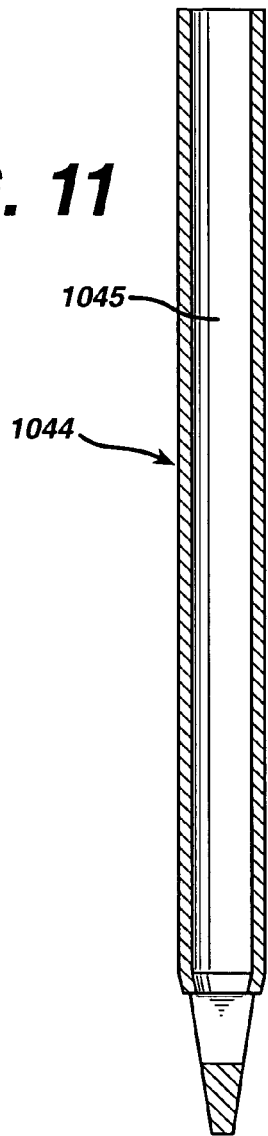
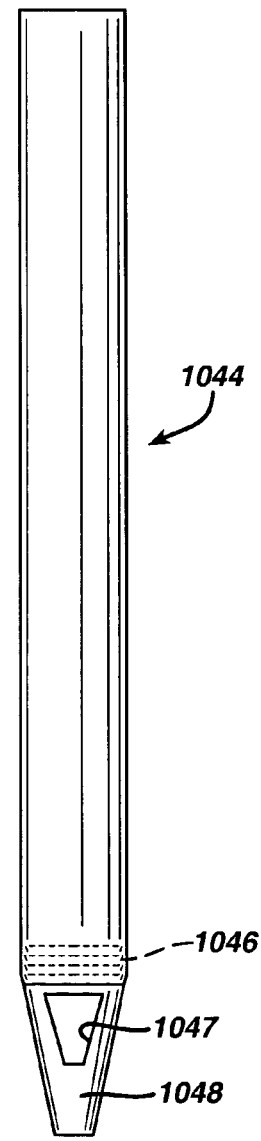

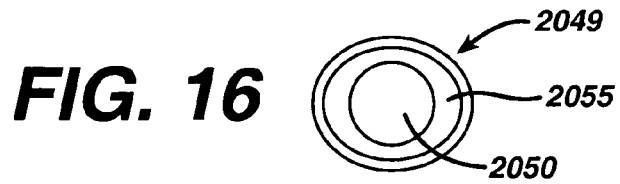
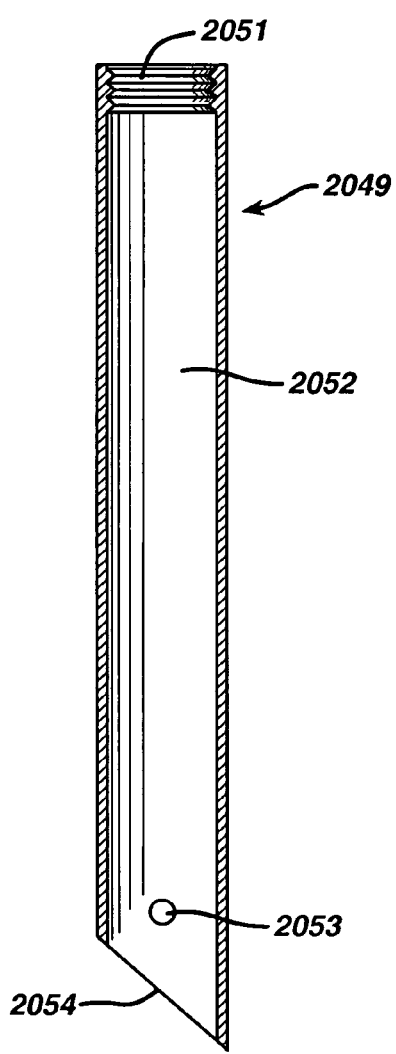
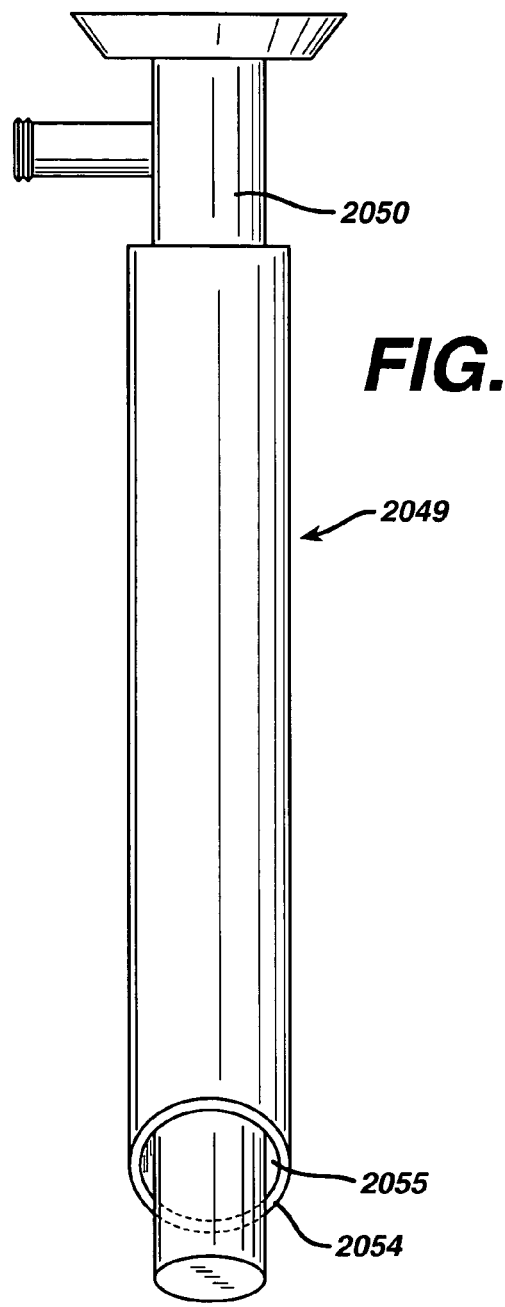

MEDICAL DEVICE FOR PROVIDING ACCESS

This application cross references related copending application Ser. No. 10/760,795 "Method of Accessing an Operative Space" filed on even date herewith.

FIELD OF THE INVENTION

This invention is related to medical devices, and more specifically to medical devices useful in performing vacuum assisted surgery, such as laparascopic surgery without insufflation.

BACKGROUND OF INVENTION

A conventional minimally invasive procedure requires the use of gas (such as carbon dioxide) insufflation to lift the tissue or body wall from internal organs, thereby separating the body wall from the internal organs to create an operative space to introduce various surgical instruments to conduct the procedure.

The following patents disclose various tools for medical or surgical applications: US20030065358A1, U.S. Pat. No. 6,120,437A1, U.S. Pat. No. 6,099,550A1, U.S. Pat. No. 5,865,802A1, U.S. Pat. No. 5,823,947A1, U.S. Pat. No. 5,797,939A1, U.S. Pat. No. 5,766,169A1, U.S. Pat. No. 5,456,684A1, U.S. Pat. No. 5,336,220A1, U.S. Pat. No. 5,186,714A1, EP0614646B1, WO0193742A2.

The following patents disclose examples of medical devices, including trocar and instrument assemblies: US200383628A1, US20030060770A1, US20030023257A1, US20030004529A1, US20030004528A1, U.S. Pat. No. 6,582,441B1, US20020198554A1, US20020183775A1, WO9410898A1, JP11089851A, JP07047076A, JP05228160A, JP04263849A, JP04253852A.

Though insufflation is commonly used, non-gas based methods have been proposed. For example, such methods may use mechanical devices wherein the tissue is lifted externally or by provided internal stirrup like supports of different mechanical assemblies to lift the tissue to create the operative space without the use of gas. One method employs a vacuum actuated tissue lifting device. The following US Patents are incorporated herein by reference for disclosure related to lifting devices and methods, including vacuum lifting devices and methods: U.S. Pat. No 6,042,539, U.S. Pat. No. 5,938,626, U.S. Pat. No. 5,893,368.

The method described in U.S. Pat. No. 6,042,539 describes a vacuum shell and provides a "dome" like operative field within the patient. An optical trocar having an obturator and cannula sleeve may be employed with such a vacuum shell. However, there can be difficulties related to use of such a trocar with vacuum assisted surgery and/or surgery without insufflation.

For instance, conventional trocars can have a working length that is not sufficient for such an application (working length can be defined as the actual length of the tubular section of a trocar below the sealing surface of the trocar). On the other hand, a trocar with an increased length may be difficult to maneuver and may restrict movement during the surgical procedure.

Additionally, it may not be desirable to use a conventional bladed trocar with a vacuum shell or other vacuum lift device, due to the possibility of accidental contact with internal organs during a first "blind" entry into the body cavity. Even if an optical obturator is employed, skill is still required to introduce and monitor the position of the trocar tip simultaneously. Also, introducing the camera assembly into the trocar obturator can result in a bulky (difficult to handle) assembly during the step of penetrating the body tissue.

Moreover, a conventional trocar which has a fixed length may not be suitable for all patients. Different patients can have different thicknesses of the abdominal wall and/or the fatty layers associated with the abdominal wall. For example, a thin or normal weight patient may require a trocar having a certain length, while a relatively obese patient may require a longer trocar.

Another problem with using a conventional trocar in vacuum assisted surgery is that when the trocar is inserted after the vacuum shell is placed on the tissue, the trocar will first cut through the perforable membrane of the shell, then pass into the patient's tissue.

If the user attempts to penetrate the body wall without the application of vacuum to the vacuum shell, body wall will tend to buckle under the penetration force, and it is possible that internal organs could be injured. On the other hand, if the conventional trocar is inserted after applying vacuum and obtaining a partial or full lift of the abdominal wall from the internal organs, the internal body cavity and organs below the abdominal wall may also "lift". Movement of the bowels under peristalsis can become sluggish due to the effects of anesthesia, which may lead to the formation of pockets of trapped gases.

These trapped gases can expand under vacuum, and may result in reduced operative space and increased gas pressure in the lumens of the bowel. Also, in the case of abdominal surgery, the time during which the intra abdominal cavity is under vacuum can lead to pulling of the diaphragm into the abdominal cavity, and can create a negative pressure in the thoracic cavity.

SUMMARY OF INVENTION

Applicants have recognized the drawbacks of the use of conventional trocars with vacuum lift devices, and that there is a need for an improved device for providing access to the inside of the body when vacuum lift devices are employed. Applicants have recognized the need for a multicomponent passageway for use as a fluid (e.g. air) conduit with a vacuum shell. Applicants have also recognized the desirability of such an assembly to be of sufficient length to take into account the gap between the tissue's external surface and the vacuum shell before vacuum application (approx. 75-100 mm) plus the tissue wall thickness to be penetrated to access the intra operative space.

In one embodiment, the invention provides a medical device comprising a multicomponent passageway for providing access to an internal space in a patient, the device comprising a first elongate, hollow member having proximal end, a distal end, and an internal lumen; a second elongate member having an open proximal end, an open distal end, and an internal lumen providing a passagweay extending therethrough; and wherein the first member is releasably attachable to the second member to provide a generally continuous internal lumen. The distal end of the first member can be positioned intermediate the proximal and distal ends of the second member upon attachment of the second member to the first member.

In another embodiment, the invention provides an assembly comprising a vacuum device for providing an operative space within a patient; and a multicomponent device for providing access from a point external of the vacuum device to a point within the patient. The multicomponent device can comprise detachable first and second members, the first member for providing a first portion of an access passageway, and the second member for providing a second poriton of an access passageway.

In another embodiment, the invention provides a method for performing a medical procedure. The method can comprise the steps of separating one portion of a patient's body from another portion of the patient's body to provide an operative space within the patient's body; and accessing the operative space through a multicomponent passageway.

The multifunctional, multicomponent passageway device can provide bi directional movement of air. The device and its method of use is such that it allows placement and access to the body cavity below the body wall before the application of vacuum with a vacuum lift device, thereby avoiding the problems related to the body cavity being under vacuum, or bowel dilation. The multimember design can provide flexibility to vary the length of the device. The device and method of the present invention can avoid potential difficulties of a first blind entry by not requiring a forced penetration or use of a sharp or pointed end to penetrate through the tissue.

A multicomponent passageway device of the present invention can help assure that the operative space created by lifting is maintained at ambient conditions (e.g. ambient pressure conditions). The device, due to its inner lumen, can also be used for passage of camera and or instruments including but not restricted to laparoscopic hand instruments during a procedure. The bi directional passage of air to maintain the ambient conditions in the body cavity may be maintained even when an instrument is passed through the device. The device of the present invention can accommodate insertion of diagnostic probes, such as, but not limited to, ultrasonic laparoscopic probes or catheter based probes through its inner lumen for intra-operative diagnostic procedures. The device can also allow removal of excised or extirpated tissue through its inner lumen during the surgical procedure (as it offers an unobstructed pathway which is devoid of any valve or flow control assembly such as is typically present in an conventional trocar) and without loss of operative space. The device according to the present invention, due to its open communication with the external ambient environment, can also provide venting of fumes which may be generated during use of electro surgical equipments for cutting or coagulation of internal tissue.

Upon release of vacuum and removal of the vacuum lift shell, the multicomponent passageway device of the present invention can also provide a channel for easy release of any air trapped in pockets of the internal body cavity. After release of vacuum and removal of the shell, the device can provide a channel for placement of a drainage catheter to drain body fluids post operatively. Also, if desired, a cannula component can be left in the incision and closed with a substantially tight cap, post operatively, to provide a port to the internal body cavity for visualization for possible bleeding or any such post operative complications.

Without being limited by theory, the multifunctional, multi member conduit device provided by the present invention can be used in medical procedures such as but not limited to gasless minimally invasive procedures using an external vacuum actuated tissue lifting device, to provide a passage way for bi directional movement of air to maintain the operative field at ambient conditions of temperature and pressure, for introducing instruments and medical camera etc, that may be used during the operative procedure i.e. diagnostic, therapeutic or surgical, for removal of extirpated/excised tissue, for clearance of fumes generated during use of electro surgical device, for cutting or coagulation etc, and for drainage of body fluids intra-operative or post operatively.

BRIEF DESCRIPTION OF DRAWINGS

FIG. 3 is a schematic plan view illustration of a cannula extension according to one embodiment of the invention, wherein the distal piercing tip is closed.

FIG. 4 is the bottom view from the distal end of the cannula extension of FIG. 3

FIG. 5 is a side elevation view of the cannula extension of FIG. 3 of the device.

FIG. 6 is a cross section view along the long axis of FIG. 5.

FIG. 11 is a schematic cross-sectional illustration of an alternate embodiment of a cannula extension member according to the present invention, the cannula extension having a non-circular, generally oval cross-section.

FIG. 13 is a side elevation view of a cannula extension having a non-circular cross-section.

FIG. 15 is a schematic illustration of a cannula having a non-circular, generally oval cross section.

FIG. 16 is a bottom view from the distal end of the cannula of FIG. 15, showing a schematic representation of a laparoscope passing through the inner lumen of the cannula, and illustrating the resulting gap to the left and right of the laparoscope due to the non-circular cross-section, thereby providing channels to the left and right of the laparoscope through which air or another instrument may pass.

FIG. 17 is a front elevation of the cannula of FIG. 15, and also schematically illustrating a laparoscope entering the proximal end of the cannula and passing through the internal lumen along the entire length of the body and exiting out at the distal beveled tip of the cannula.

DETAILED DESCRIPTION OF THE PREFERRED EMBODIMENTS

By the term "elongate" or "elongated" it is meant that a component or member has a length at least three times its width (e.g. a cylinder with a length at least three times the outer diameter).

The terms "procedure" or "operative procedure" mean medical procedures, including without limitation exploratory, diagnostic, therapeutic, surgical, ambulatory or mobile, emergency, and post mortem procedures, either open or laparoscopic or laparoscopically assisted.

The term "operative space" means any working space created within the body, such as below any tissue or an organ by relative separation, such as by lifting partially or fully one body structure relative to another.

The term "distal" is used to refer to the portion, part, end, or tip of a component or member which is away from the user, while the term "proximal" is used to describe the portion, part, end, or tip which is closer to the user of the device.

By "releasable attachment" and "releasably attachable" it is meant two or more components can be repeatedly joined and separated without breaking, distorting, damaging, or impairing the function or form of the components.

For purposes of explanation, the figures and the description are provided with respect to an example of a procedure employing lifting of the abdominal wall, but it will be understood the invention can have applicability to other parts of the patient's body. In particular, but without limitation, the present invention can have applicability to procedures in which external portions of the body are lifted with respect to internal portions of the body to create an operative space.

While the vacuum shell and vacuum are described as examples of a mean of lifting the body tissue, it will be understood the appended claims are not limited to applications involving the vacuum shell disclosed and illustrated below. For example, other lifting methods, including mechanical, electromechanical, gas based or non gas based can be employed with the device of the present invention.

While the description and figures depict threaded engagement features for releasably attaching components, it will be understood other suitable engagement features can be employed, including without limitation friction fitting, snap fit features, press fit features, and electrical or electro mechanical attachment means.

Figure 1:
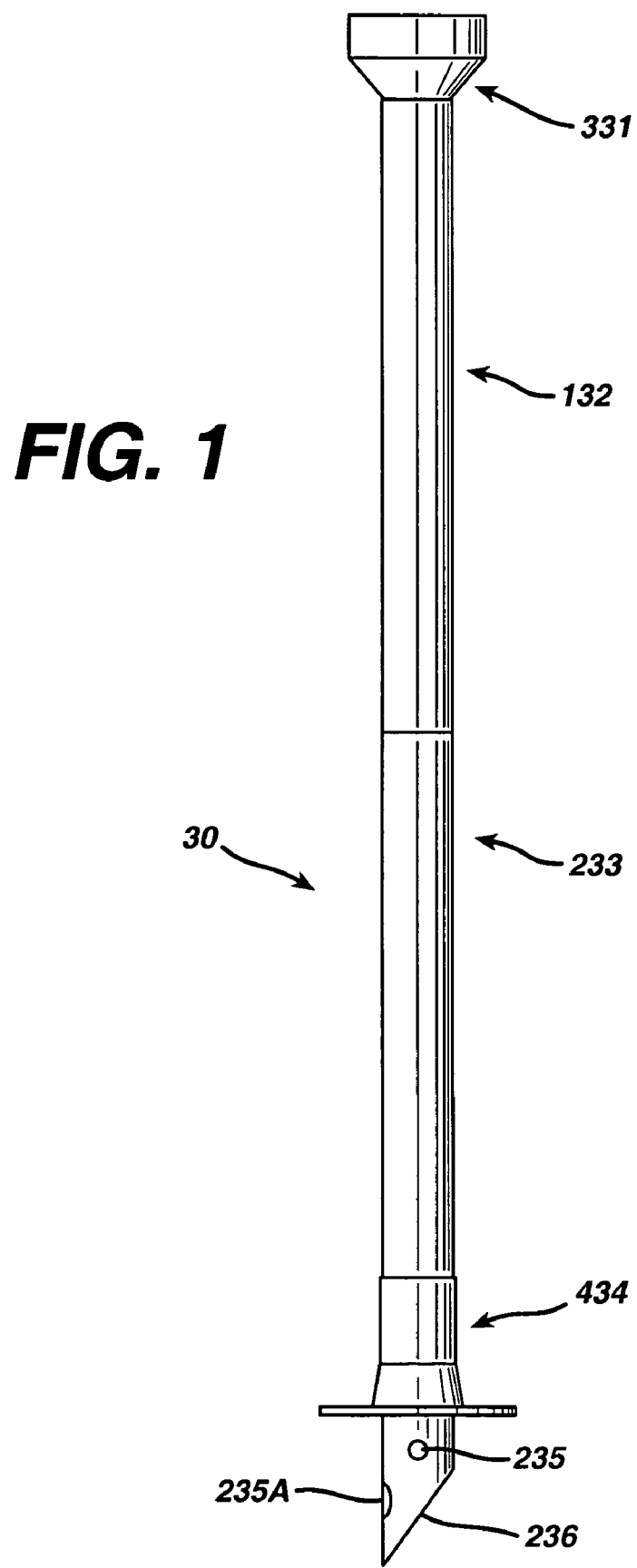
FIG. 1 is a schematic plan view illustration of a medical device according to one embodiment of the present invention.
Figure 2:
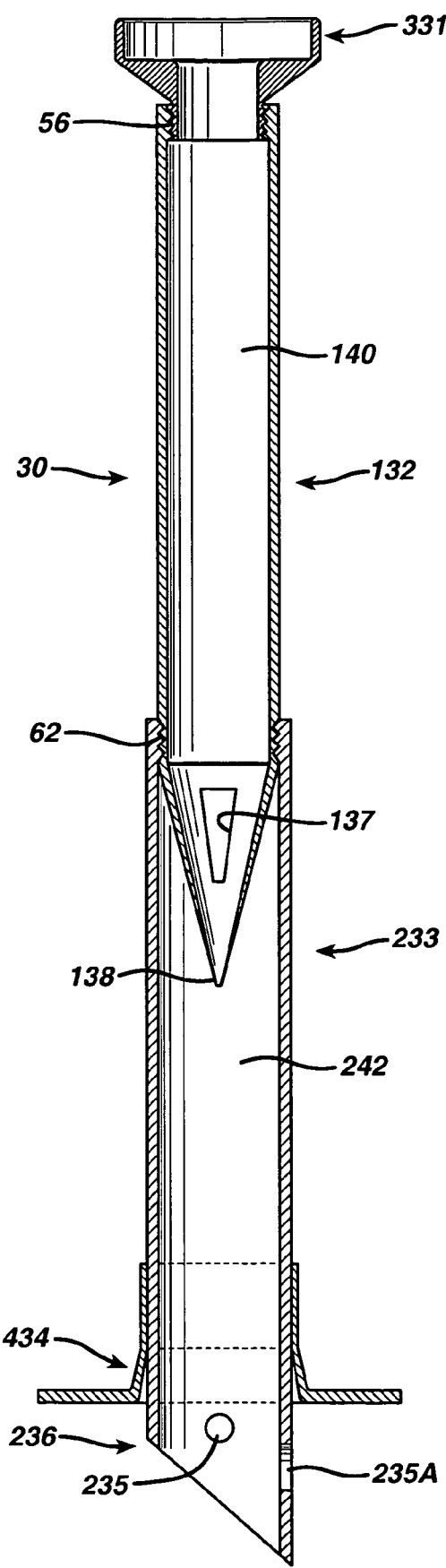
FIG. 2 is a cross section view along the long axis of the device in FIG. 1.

An assembled medical device 30 according to one embodiment of the present invention is shown in FIGS. 1 and 2. The medical device 30 can include a first elongate, hollow member and a second elongate, hollow member which are releasably attachable, one to the other. The first elongate member can comprise a cannula extension 132. The second elongate member can comprise a cannula 233. The medical device 30 can also include a third member, which can be releasably attacheable to one or both of the cannula extension 132 and the cannula 233. In FIGS. 1 and 2, the third element can comprise a cap 331. The device 30 can also include a sleeve 434 for providing sealing.

Each of the cannula extension 132, cannula 233, and cap 331 can be formed of any suitable biocompatible material. In one embodiment, the members 132, 233, and 331 can be formed of a relatively rigid or semi rigid non collapsible biocompatible material which can be translucent, transparent, or opaque. In one embodiment, each of the members 132, 233, and 331 can be transparent. Each member may be made by extrusion or injection molding or any suitable plastic processing method or other suitable manufacturing method. In one embodiment, each of the members 132, 233, and 331 can be formed of polycarbonate, impact modified acrylic, actyl butydene styrene (ABS), or polyethyl ether ketone (PEEK).

The medical device 30 can also comprise the fourth member, sealing sleeve 434. Sealing sleeve 434 can be formed of a relatively flexible material, such as a flexible polyurethane, silicone, polypropylene, polyisoprene, or rubber. Sealing sleeve 434 can be disposed about the outer surface of cannula 233, such that sleeve 434 fits snugly about the outer diameter of the cannula 233.

Referring to FIGS. 3-6 and FIGS. 11-14, the cannula extension 132 can have any suitable cross-section, including circular and non-circular cross-sections. The cannula extension 132 can have an open proximal end 142 and a distal end 144 which may be open or closed. The cannula extension can include an internal lumen 140 which extends from a proximal end 142 to a distal end 144 of the cannula extension 132. Both the cannula extension and the internal lumen can have circular cross sections, as shown in FIG. 3-6, or non-circular, generally oval cross-sections as shown in FIGS. 11-14. Alternatively, the cannula extension 132 could have a generally cylindrical outer surface, and the inner lumen 140 could have a non-circular cross-section. The cannula extension 132 is shown as a single, unitary component, but cannula extension 132 could be in the form of multiple components if desired.

The cannula extension 132 can have a length (as measured from the proximal end to the pointed tip 138) of at least about 100 mm (millimeters), and in one embodiment the length of the cannula extension can be between about 100 mm and about 175 mm, and can be at least about six times the outer diameter of the cannula extension 132. The outer diameter of the cannula extension 132 can be about 15 mm, and the inside diameter of lumen 140 can be about 12.75 mm, such as to accommodate 10 mm sized hand instruments. Without being limited by theory, when 10 mm sized instruments are to be employed, it is believe that it can be desirable to have an inner diameter of at least about 12.75 mm to provide flow area around instruments introduced through lumen 140. If a non-circular lumen is employed, a inside lumen with an inside dimension of at least 12.75 mm can be employed to provide flow around such an introduced instrument (e.g. if an oval or elliptical shaped cross section is employed, it can be desirable to have the major axis be at least about 12.75 mm, and the minor axis to be at least about 11 mm). It will be understood that the outside and inside diameters may be varied for different applications (e.g. reduced for smaller diameter 5 mm or 3 mm minimally invasive instrument sets).

The cannula extension 132 can include a pointed tip 138 associated with distal end 144. The pointed tip 138 can be provided for piercing through a portion of a vacuum shell membrane. The main body portion of cannula extension 132 can have a generally cylindrical outer surface, and a distal portion of cannula extension 132 can have a tapered, generally conical outer surface as shown in FIGS. 3 and 5. One or more lateral openings 137 (or "windows") can extend through the wall of the tapered distal portion of the cannula extension 132 to provide communication from the inner lumen 140 through the outer surface of the cannula extension 132. The openings 137 can be positioned proximally of the pointed tip 138 at distal end 144, just above the pointed tip 138. In FIG. 3, two openings 137 are positioned about 180 degrees apart around the outside surface of the tapered distal portion of the cannula extension 132.

The openings 137 can have any suitable shape. It can be desirable that the openings 137 have a combined surface area of at least about 30 square millimeters to provide sufficient air passage, such as to help in avoiding the occurance of a negative pressure (vacuum) inside the body cavity.

Cannula extension 132 can also include an attachment portion 139 for releasably attaching the cannula extension 132 to the cannula 233. The attachment portion 139 can be in the form of external screw threads for allowing the cannula extension 132 to be releasably attached to the cannula by threaded engagement in screw-like fashion, though other attachment means (e.g. latching mechanisms, press fits, snap fits, and other releasable fastening devices) could be employed. The attachment portion 139 can be provided to prevent leakage of air at the juncture of the cannula extension 132 and the cannula 233. The cannula extension 132 can also include an attachment portion 141 positioned at the proximal end 142 of the cannula extension 132. The attachment portion 141 can be provided to releasably attach the cap 331 to the proximal end of the cannula extension 132. The attachment portion 141 can be in the form of internal screw threads, as shown in FIG. 6.

Figure 3A:
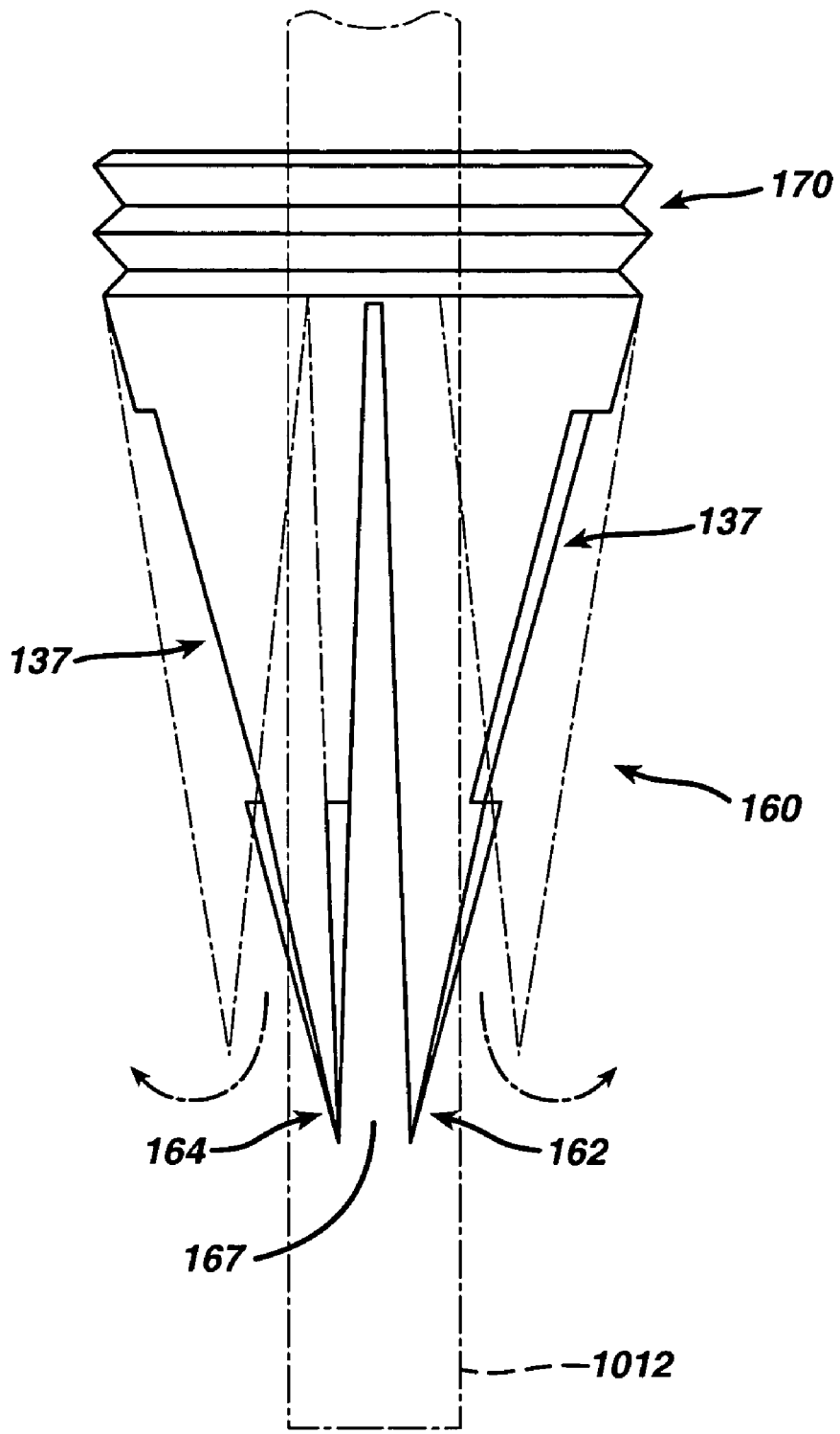
FIG. 3A is schematic illustration of the distal end of the cannula extension according to an alternative embodiment of the present invention, the cannula extension having a flexible distal portion with an open distal end, such as along a slit, to provide for instrument passage.

FIG. 3A illustrates an alternative embodiment of a cannula extension 132 having an open distal end. In FIG. 3A, the cannula extension 132 is shown having a bifurcated distal portion 160 comprising a first tip portion 162 and a second tip portion 164. The bifurcated distal portion 160 can be formed by cutting or otherwise forming the distal end of the cannula extension 132. For instance, the distal end of the cannula extension 132 can be cut or formed to have a slit 167 extending generally parallel to the axis of the cannula extension 132 to generally bisect the distal end of the cannula extension 132. The distal portion 160 can be formed of a flexible material, such rubber, silicone rubber, or a suitable flexible polymeric material so that tip portions 162 and 164 can be easily spread apart (as shown in phantom in FIG. 3A). FIG. 3A illustrates how bifurcated distal portion 160 can be separated to allow introduction of a laparoscope 1012 (shown in phantom) therethrough.

Figure 3B:
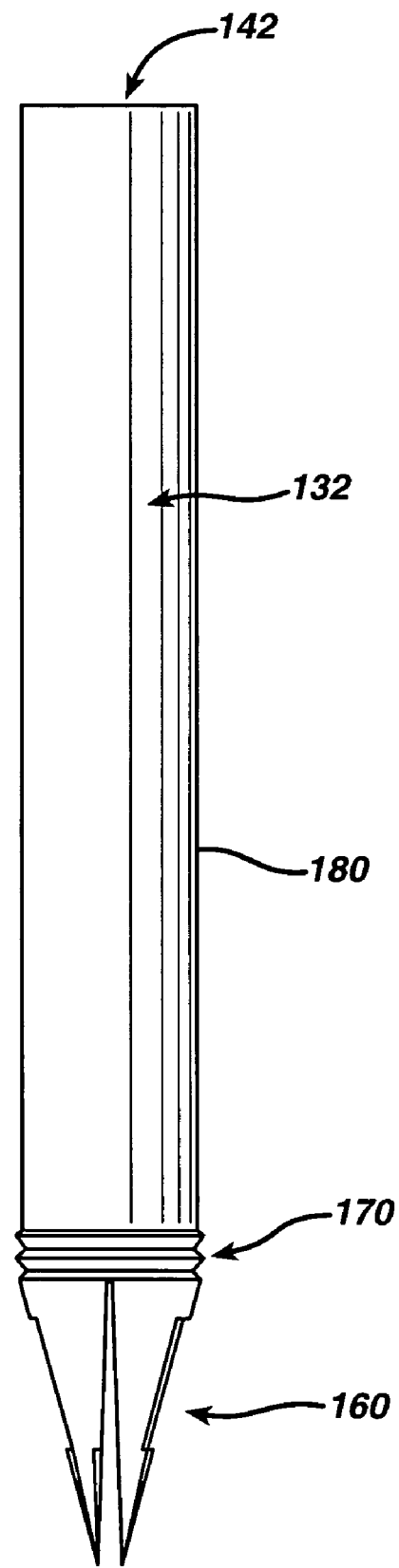
FIG. 3B is a schematic illustration showing the flexible distal portion of FIG. 3A joined to a proximal tubular portion of the cannula extension.
Figure 7:
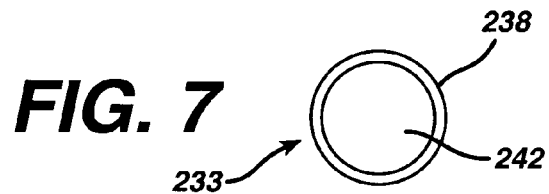
FIG. 7. is a top view from proximal end of a cannula according to one embodiment of the present invention.

Referring to FIG. 3B, the proximal portion of the cannula extension 132 can be formed from a generally cylindrical, relatively rigid and generally transparent polycarbonate tube 180, and the distal portion 160 can be formed of rubber or other relatively flexible material, with distal portion 160 being joined to the tube 180 at a flexible hinge portion 170. Hinge portion 170 can have a corrugated or bellows-like wall construction to provide for bending of distal portion 160 relative to the polycarbonate tube 180. Hinge portion 170 can be attached to tube 180 by any suitable method, including without limitation by interference fit, press fit, snap fit, adhesive, or by threaded engagement. If desired, one or more surfaces on the distal portion 160 can be employed to provide sealing engagement with an abutting surface on the cannula 233. For instance, one of the inclined surfaces on the hinge portion 170 can be used to form a seal against an abutting surface on the cannula 233. Also, in an alternative embodiment, the grooves of the hinge portion 170 can be employed to mate with complimentary grooves which can be provided on the cannula extension 132 to provide releasable attachment of the cannula extension 132 and the cannula 233.

Figure 8:
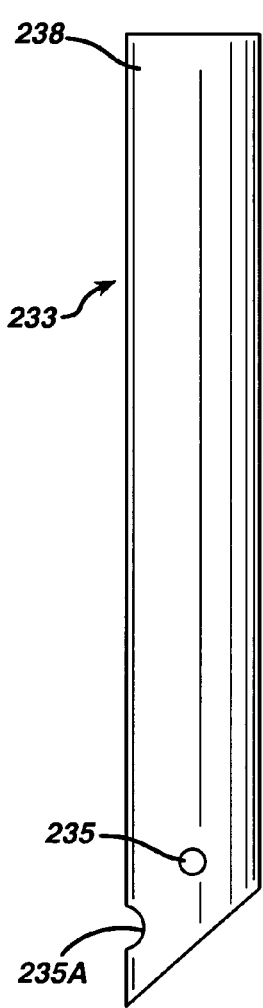
FIG. 8 is a schematic side elevation view of a cannula according to one embodiment of the present invention.
Figure 9:
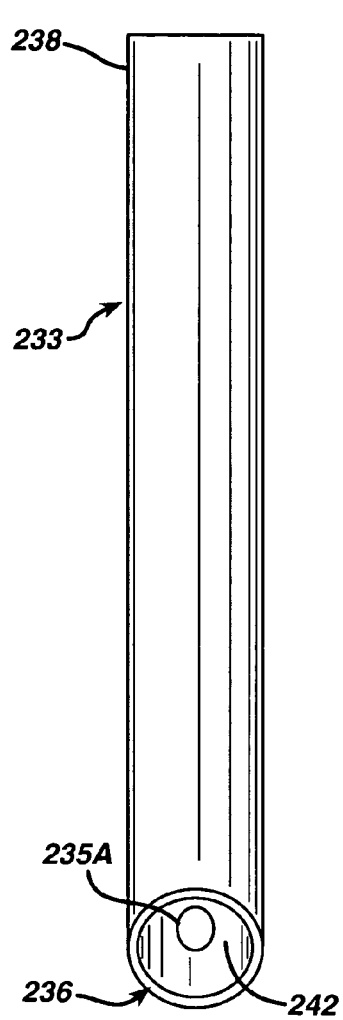
FIG. 9 is the front elevation view of the cannula of FIG. 8.
Figure 10:
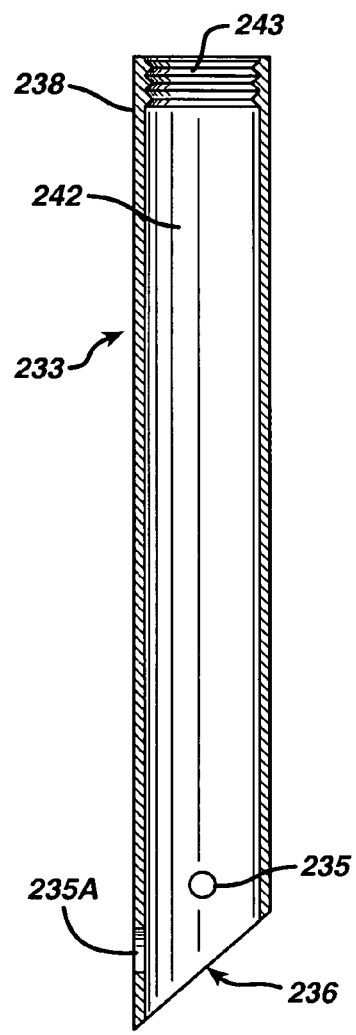
FIG. 10 is the cross section view of the cannula along its long axis.
Figure 12:
FIG. 12 is the top view from the proximal end, showing the generally oval cross section of the cannula extension in FIG. 11.
Figure 14:
FIG. 14 is a bottom view from the distal end of the cannula extension of FIG. 13.

FIGS. 2 and 7-10 illustrate a cannula 233 according to one embodiment of the present invention. The cannula 233 can have any suitable cross sectional shape (e.g. circular or non-circular, such as oval), which cross-sectional shape can be the same as, or different from the cross sectional shape of the cannula extension 132. The cannula 233 can have a proximal end 238 and a distal end 236, with an internal lumen 242 extending from the proximal end to the distal end. The cannula 233 can have any suitable cross sectional shape, including circular and non-circular cross-sections (e.g. oval) as shown in FIGS. 7-10 and FIGS. 15, 17. The distal end 236 can be beveled to form a beveled tip, as shown in FIGS. 8-10, for easy entry through any incision. The wall thickness of the cannula can be uniform or can vary along the length of the cannula. For instance, the wall thickness at the distal end 236 may be varied for easy penetration through an incision.

The cannula 233 can have a length of at least about 100 mm, and in one embodiment the cannula has a length between about 100 mm and about 175 mm. The length of the cannula 233 can be greater than, less than, or substantially the same length as that of the cannula extension 132. When 10 mm size instruments are to be introduced through the cannula 233, the outside diameter of the cannula can be about 15 mm, and the inside diameter of the internal lumen 242 can be at least about 12.75 mm. The dimensions of the cannula 233 can be varied, such as by being reduced for use with smaller 5 mm or 3 mm instrument sets. Generally, it is desirable that the outer diameter and shape of the cannula and the cannula extension be substantially the same to avoid leakage through the vacuum shell membrane. In one embodiment, the minimum inner diameter of both the cannula and the cannula extension can be at least about 12.75 mm to provide a continuous, uninterrupted air passageway with or without instruments extending through the cannula and cannula extension.

The cannula 233 can include one or more lateral openings through the wall of the cannula, such as circular eyelets 235. For instance, two or more circular eyelets 235 can be spaced at generally equal angular intervals around the circumference of outside surface of cannula 233. If desired, a relatively larger eyelet 235A can be positioned along the longest side of the beveled tip 236, as shown in FIG. 2. The eyelets extend through the wall of the cannula and provide fluid (e.g. gas such as air) communication from internal lumen 242 to the outside of the cannula. The eyelets can be positioned proximally of the beveled tip, and in one embodiment the eyelets 235 can be spaced a maximum of about 5-10 mm from the edge of the beveled tip as measured parallel to the axis of the cannula 233. The eyelets can provide an air passageway for air from cannula extension 132 through cannula 233 and into the internal body cavity in the event the distal end 236 of cannula is blocked for any reasons (e.g. such as by end 236 being positioned against a tissue or organ mass).

The cannula can also include an attachment portion 243, such as internal grooves or an internal threaded portion for releasably attaching the proximal end of the cannula 233 to the cannula extension 132. Attachment portion 243 can have screw threads, grooves, or other features for releasably engaging with external surface features (such as external screw threads) on cannula extension 132. Attachment portion 243 can also be used for releasabley attaching the cap 331 to the proximal end of cannula 233.

Figure 18:
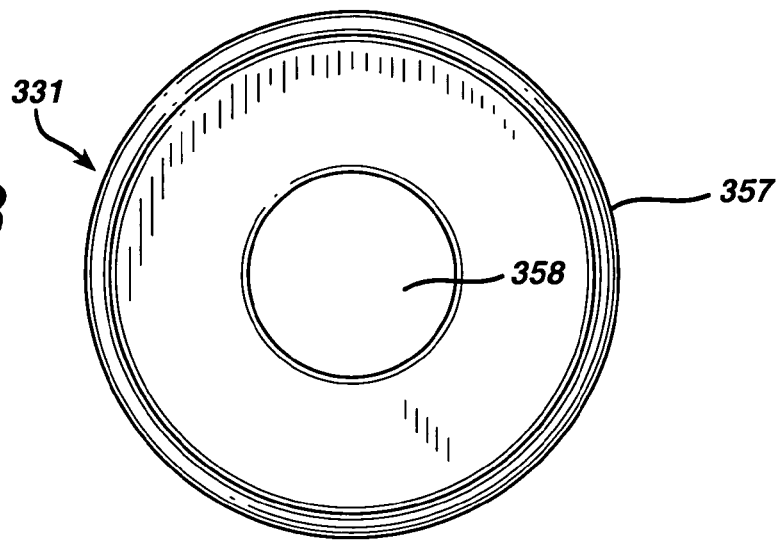
FIG. 18 is a top view of a cap according to one embodiment of the present invention.
Figure 19:
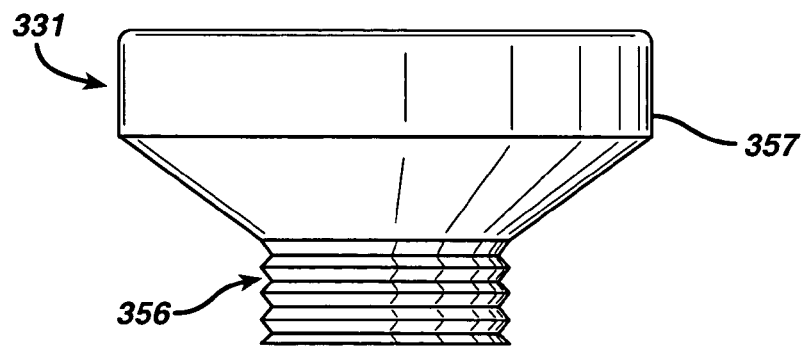
FIG. 19 is a front elevation of the cap of FIG. 18.
Figure 20:
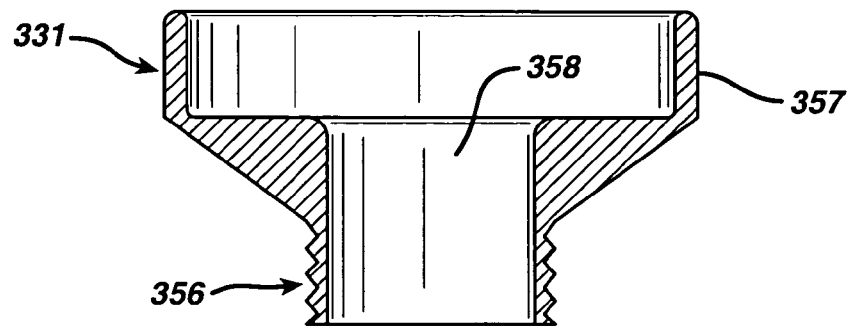
FIG. 20 is a cross section of the cap of FIG. 18.

FIGS. 18-20 illustrate a cap 331. The cap 331 can include a main body portion 357 and an attachment portion 356 such as an external threaded portion. The relatively large outside diameter of body portion 357 provides a handle for gripping by the user. External threaded portion 356 can be formed to engage the threaded portions of the cannula extension 132 and the cannula 233, such that cap 331 can be releasably attached to the proximal end of either cannula extension 132 or cannula 233. The cap 331 can have an internal, central bore 358 which can be of substantially the same size (e.g. same diameter) as the internal lumen 140 and the internal lumen 242. The central bore 353 together with internal lumen 140 and internal lumen 242 can provide a continuous air passageway from outside the patient to the internal operative space within the body.

Figure 27:
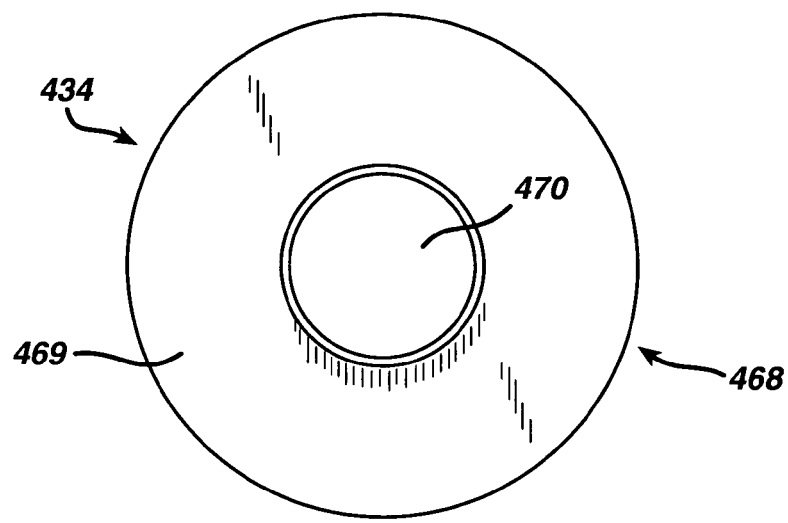
FIG. 27 is a bottom view of a sealing sleeve showing a flange surface area which can be provided with an adhesive.
Figure 28:
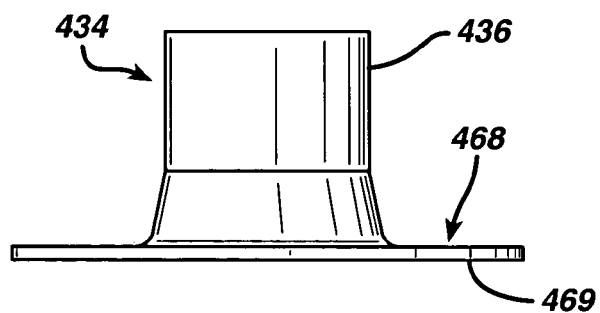
FIG. 28 is the front elevation of the sealing sleeve.
Figure 29:
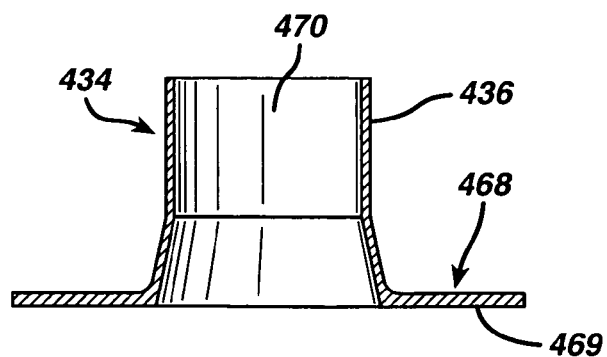
FIG. 29 is a cross section view of the sealing sleeve.

FIGS. 27-29 illustrate a sealing sleeve 434 according to one embodiment of the present invention. The sleeve 434 has a generally cylindrical body portion 436 and a flange portion 468 extending radially from the distal end of the cylindrical body portion 436. A central bore 470 extends through sleeve 434. Central bore 470 can be sized so that sleeve 434 can snugly fit around and slide along the length of the outside surface of cannula 233. The sleeve can be formed of a relatively flexible material such as rubber, so that flange portion 468 can contour to contours of the patient's body. A bottom surface 469 of the flange 468 can be coated with or otherwise provided with an adhesive, such as a pressure sensitive adhesive coating or other suitable adhesive. A release liner (not shown) can be used to cover the adhesive prior to time of use, and the release liner can be pealed from the flange surface at the time of use to expose the adhesive coating. The adhesive coating provided on surface 469 can be used to temporarily attach the sleeve 434 to an outer surface of the patient's body, so that flange 468 helps in supporting the cannula 233 when the cannula is inserted into an incision in the patient's body. The surface 469 can also be provided with a medicinal substance, such as a medicinal substance selected from the group of substances consisting of hemostatic substances, anti-microbial substances, antibacterial substances, pain reducing agents, and combinations thereof.

FIGS. 11-14 illustrate an alternative embodiment of a cannula extension labeled with reference number 1044. Cannula extension 1044 is shown having a generally oval shaped cross-section and an internal lumen 1045 having a generally oval shaped cross-section. FIGS. 15, 16 & 17 illustrate an alternative embodiment of a cannula labeled with reference number 2049. Cannula 2049 is shown having a generally oval shaped cross-section and having an internal lumen 2052 having a generally oval shaped cross-section. The cannula extension 1044 can be releasably joined to cannula 2049

Employing internal lumens having oval cross-sections or other non-circular cross-sections may be advantageous for accommodating instruments having a large width dimension that can be inserted so that the large width dimension is aligned with the long axis of the oval cross-section. An oval cross-section may also be useful for simultaneously receiving multiple instruments, such as in side by side relationship. An oval cross-section may also be useful in retrieving larger tissue samples through the cannula 2049. An oval cross-section may also aid in reducing the stretching of tissue around the incision in the patient. Referring to FIGS. 16 and 17, the non-circular cross-section of lumen 2049 can also leave gaps 2055 on either side of a circular instrument 2050 inserted in the lumen, so that an air passage is maintained through the cannula 2049 even when the instrument is positioned in the lumen 2049. The relatively large cross-section provided by an oval shape can also provide for a larger flow volume through the lumen 2049, which may be desirable in applications where fast air pass or a large quantity of air is required. For example, when the tissue is lifted with a vacuum shell using a very high capacity vacuum, if the air passageway is not large enough, a partial vacuum effect may be created inside the body cavity for a short period of time. A non-circular design such as an oval shaped cross-section can avoid such a partial vacuum effect by providing gaps 2055 around the instrument 2050, as well as providing a large flow area when the instrument is not present.

An non-circular cross-section such as an oval cross-section can be employed to accommodate an instrument which would not pass through a circular cross-section having an internal diameter comparable to the minor dimension of the non circular cross-section. Alternatively, an oval cross section may also be employed to accommodate multiple instruments of smaller profiles simultaneously. An oval or non-circular cross-section may also be useful for use in extracting relatively large excised tissue through the cannula and cannula extension. The non-circular cross-section can cause the tissue to be squeezed in one direction while allowing it to expand in the other when passing through such a cannula and cannula extension. Without being limited by theory, an oval or similar non-circular cross-section may also reduce the stretching of the tissue around the incision 59 through which it passes. Further, a non-circular shape may be employed to provide larger area for passage of air and thus help in applications where fast air pass or a larger quantity of air passage is desired (for example when the tissue is lifted by using a very high capacity vacuum, if the lumen of device is not large enough, a partial vacuum effect may be created inside the body cavity for a short period of time. A non-circular lumen cross-section can be employed to avoid such a partial vacuum by providing a relatively large flow area even when the instrument 51 is present.

Figure 21:
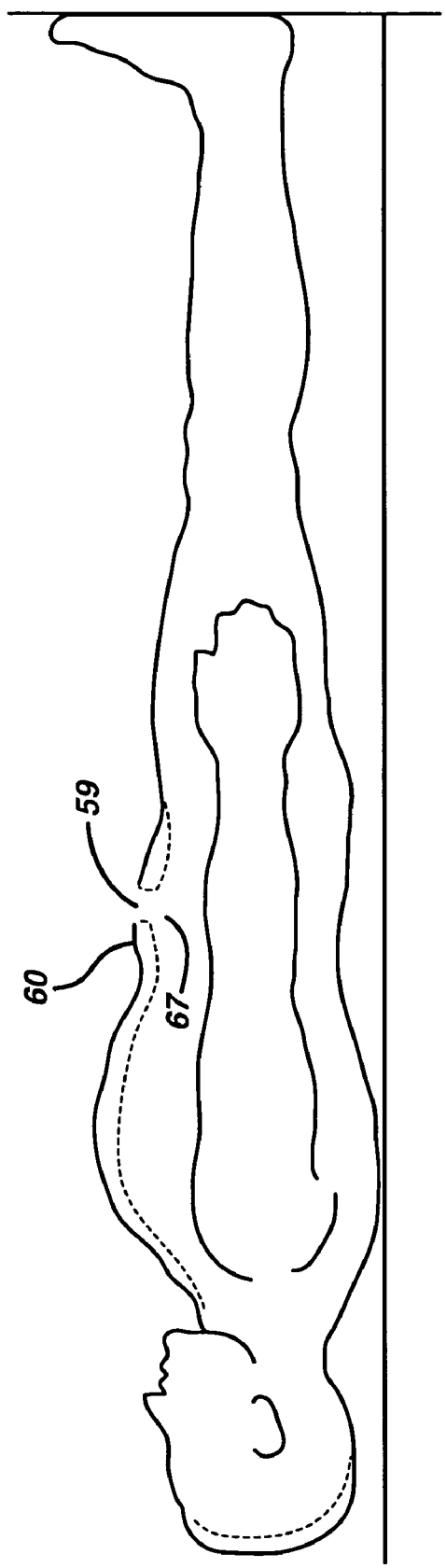
FIG. 21 is a perspective view of a patient lying on a procedure table and an incision made through a body wall such as the abdominal wall to gain access to a body cavity such as the abdominal cavity wherein the operative space is to be provided.
Figure 22:
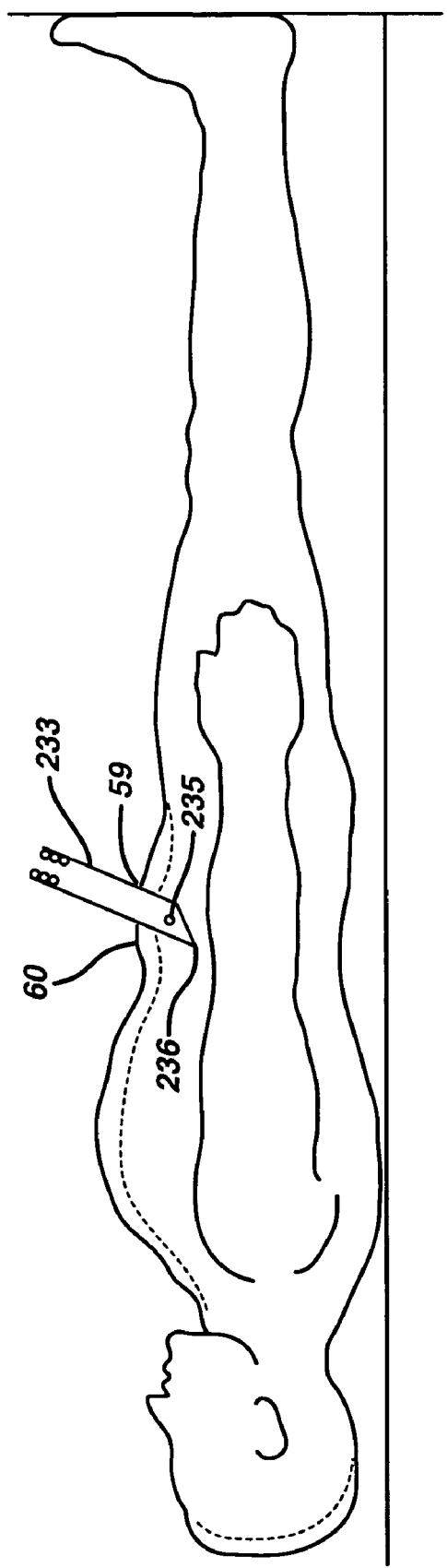
FIG. 22 is a schematic illustration showing a cannula of the present invention positioned to extend through the incision in the body wall with the beveled end of the cannula positioned in the body cavity, and with air passageways in the form of eyelets disposed proximally of the beveled end also positioned below the body wall and in the body cavity.

The method of use of the multifunctional device 30 is illustrated in FIGS. 21-26. As shown in FIG. 21, with the patient lying on his/her back during the procedure, an incision 59 can be made through the body wall 60 (or other tissue which is to be lifted) to obtain access to the internal body cavity 67. Once the incision is made, it is kept open using artery forceps or retractors and the cannula 233 of the multifunctional device 30 can be introduced into the body cavity 67 such that beveled tip 236 and the multiple eyelets 235 are all disposed inside the body cavity. Markings can be provided on the external surface of the cannula 233 to help the surgeon determine the depth of insertion to avoid leakage of air or slippage of the cannula extension into the body cavity. If desired, the outside surface of the cannula 233 can include grooves or ridges (such as coaxial ring grooves along a length of the outside surface of the cannula 233) to help prevent slipping of the cannula 233 in the incision, and to help provide an air seal between the borders of the incision and the outer surface of the cannula 233.

Once cannula extension is inserted to the required depth, incision may be sutured using a purse string technique to make it air tight around the cannula extension 233. Additional the sealing sleeve 434 can be slid downwards over the cannula extension 233 towards the incision 59. The protective release liner can be removed from the adhesive coated surface 469 of flange 468 on the sleeve 434. The flange 468 can then be pressed onto the external surface of body wall 60 surrounding the incision 59 to make it airtight. In addition to the adhesive coating, the surface 469 may also be coated with other active agents such as anti microbial agents, wound healing agents, hemostatic agents, and the like for additional activity and use of the sealing sleeve. Alternatively instead of an adhesive coating a gel like coating may also be used to make the seal substantially air tight. In addition to providing sealing at the incision, the sleeve 434 can also help stabilize the cannula extension 233 in place.

Figure 23:
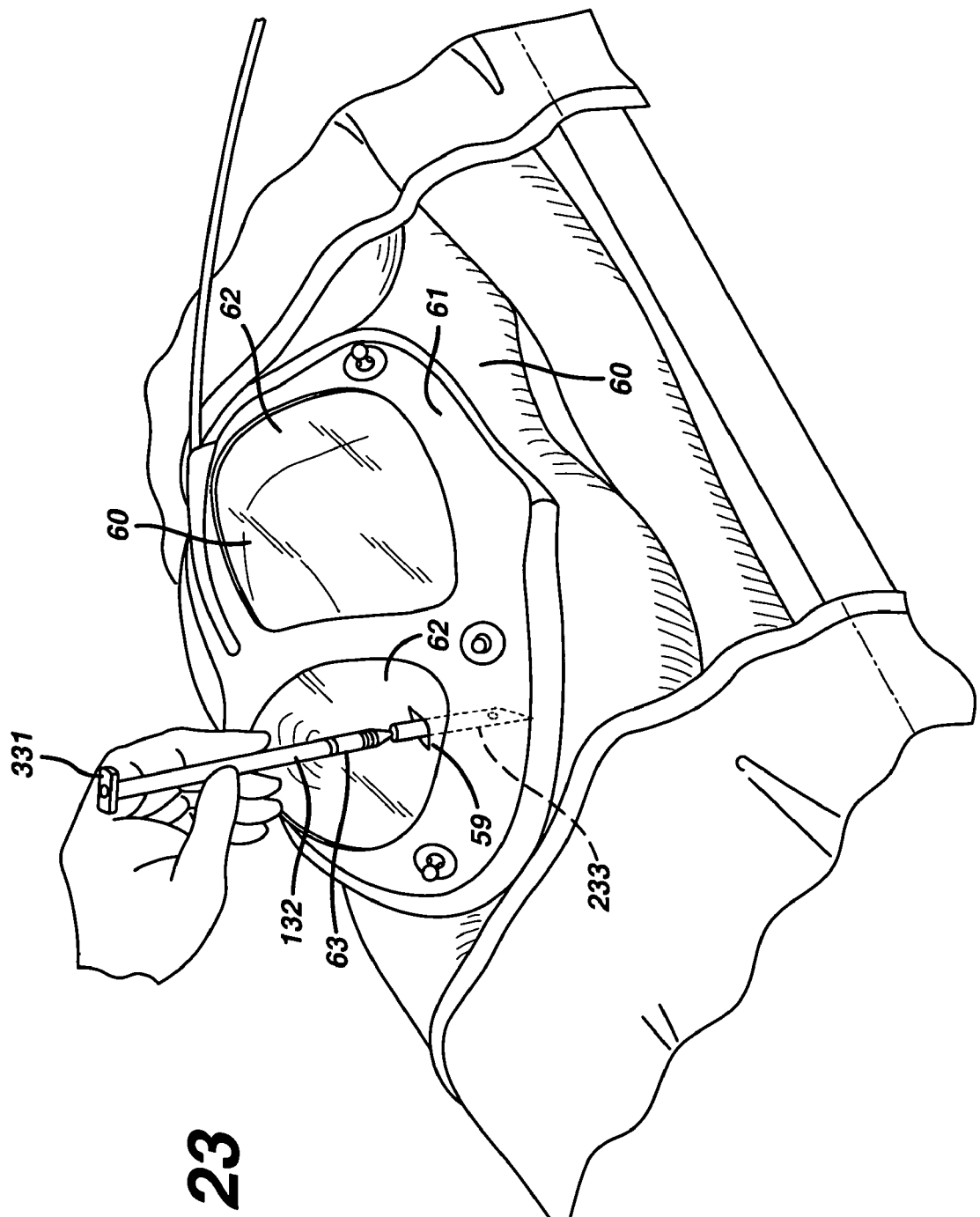
FIG. 23 is a perspective view of the vacuum shell to be used to lift the body wall/tissue positioned over a portion of the patient through which the cannula extends, wherein the distal piercing tip of the cannula extension is depicted as being used to penetrate a perforable membrane of the vacuum shell, and showing positioning the distal tip of the cannula extension to align with the proximal end of the cannula, such that the distal tip of the cannula extension can be positioned within the cannula, and such that the cannula extension can be releasably attached to the cannula.

Once the incision is made sufficiently airtight, the vacuum shell 61 is placed on the outside surface of the body wall 60 (e.g the outer skin off the abdomen) such that at least one perforable membrane 62 of the vacuum shell is above the cannula extension 233 as shown in FIG. 23. The pointed tip 138 of the cannula extension 132 can be used to penetrate the perforable membrane 62 of the vacuum shell to form an opening 63 in the membrane 62 (FIG. 23). The cap 331 can be joined to the cannula extension 132 and can serve as a handle to provide grip for advancement of the cannula extension 132. The cannula extension 132 can then be pushed distally toward the incision and aligned with the proximal end of the cannula 233. The pointed tip 138 can be inserted into the cannula 233, and the extension 132 can be releasably attached to the member 233, such as by threaded engagement, friction fit, or any other suitable releasable attachment mechanism, thereby providing an assembly of the cannula 233, the extension 132, the sleeve 434, and the cap. With the components assembled, vacuum can be provided to the vacuum shell. 61.

Figure 24:
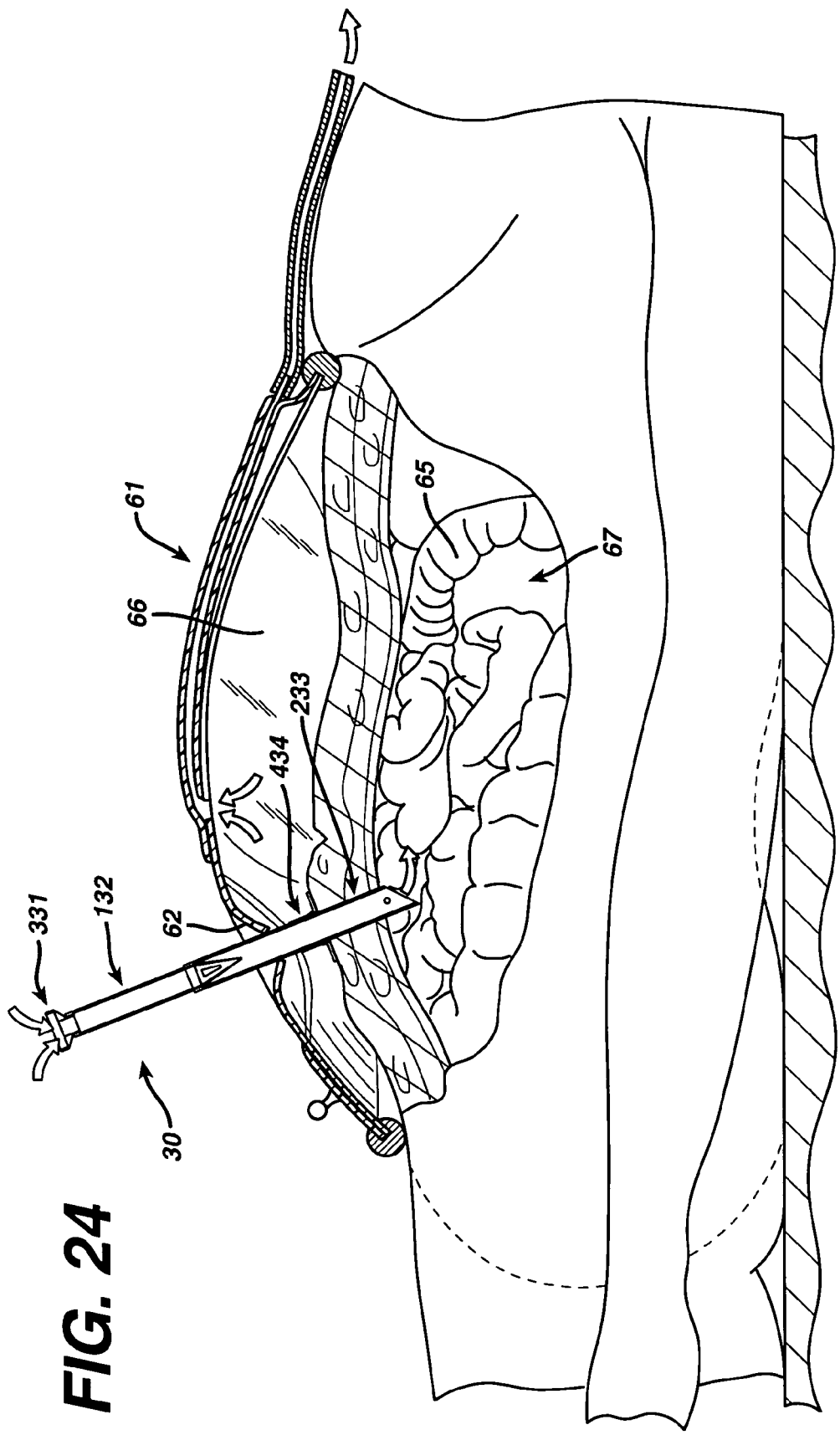
FIG. 24 is a schematic illustration of the multiple component device of the present invention assembled and in operative association with the vacuum shell, with vacuum being provided to lift the patients body wall and provide an operative space intermediate the body wall and internal organs, with arrows in various locations depicting the direction of flow of air, such as for instance, air entering the body cavity through the air passageway provided through the assembled cap, cannula extension, and cannula of the present invention.

Vacuum applied using the shell 61 results in air being drawn from the space 66, as illustrated by the arrows in FIG. 24. The vacuum causes body wall 59 to lift upwards towards the shell 61. Simultaneously, air from the external ambient environment can enter body cavity 67 through device 30, by passing through the inner lumens of the hollow cannula 233 and the hollow cannula extension 132. Air can enter into the device 30 through the cap 31, pass through its inner lumen 458, then through inner lumen 140 of cannula extension 132. The air can then pass through the distal end of extension 132 by passing through the fluid passage windows 137, to enter lumen 242 of the cannula 233. The air can then flow into the body cavity through the beveled tip 236 and/or through the plurality of eyelets 235/235A.

The amount of air drawn into the body cavity depends, to some extent, on the size of the inner lumen of the device 30 as assembled, as well as the size of the windows 137 and the opening at the beveled tip 236, and the rate and level of vacuum applied to the vacuum shell. By providing a continuous fluid passage through the assembled device 30, the air drawn into the body cavity 67 will be sufficient to balance the effect of the vacuum applied by the vacuum shell and to maintain body cavity 67 at an ambient condition of pressure and also avoid any lifting or bloating or distension of internal organs 65 below the body wall.

Cap 31 can be employed to help avoid slippage of the device 30 into the body cavity or below the shell 61. During the entire procedure the multifunctional, multicomponent device 30 can serve to provide communication path for fluids and/or devices from the external environment outside the patient to the internal body cavity 67.

Figure 25:
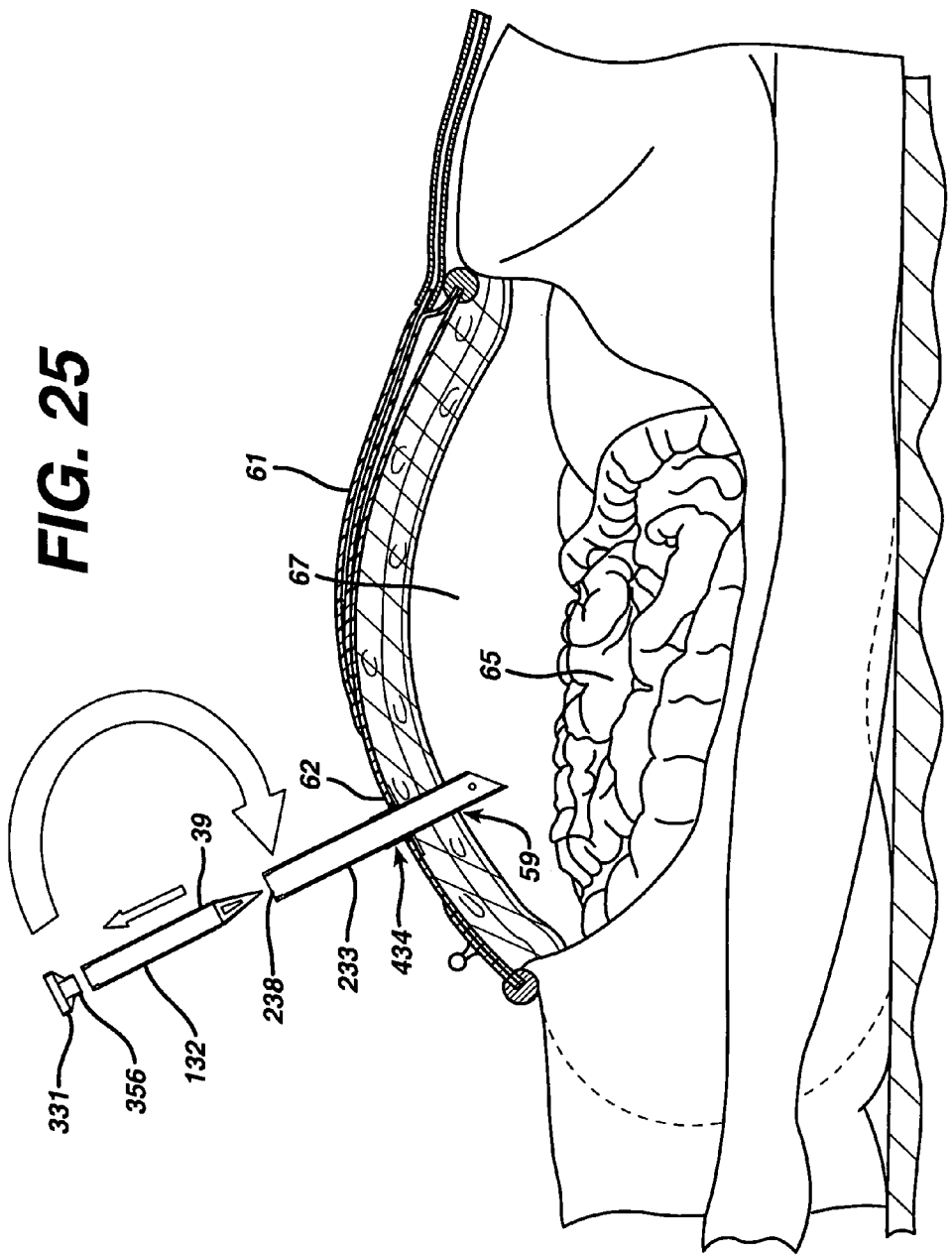
FIG. 25 is a perspective view, which schematically illustrates the operative space created by the use of vacuum shell and the multifunctional access device of the present invention, FIG. 25 illustrating detaching the cannula extension from the cannula once lift is provided, and the cannula partially withdrawn in a proximal direction to position the beveled distal end of the cannula extension just below the body wall.

As complete vacuum lift is obtained, the external surface of the body wall 60 can contact the internal surface of the vacuum shell 61 as shown in FIG. 25. Due to this lift an operative space is created in the body cavity 67. The device 30 as assembled in FIG. 24 can then be retracted proximally as shown in FIG. 25 until the junction of the cannula 233 and the cannula extension 132 is postioned externally of the perforable membrane 62 of the shell 61. Cap 331 can be grasped for pulling the device 30 proximally. Depth markings on the external surface of cannula 233 can be used to a minimum desirable length of the cannula 233 remains within the space in the body cavity 67.

Figure 26:
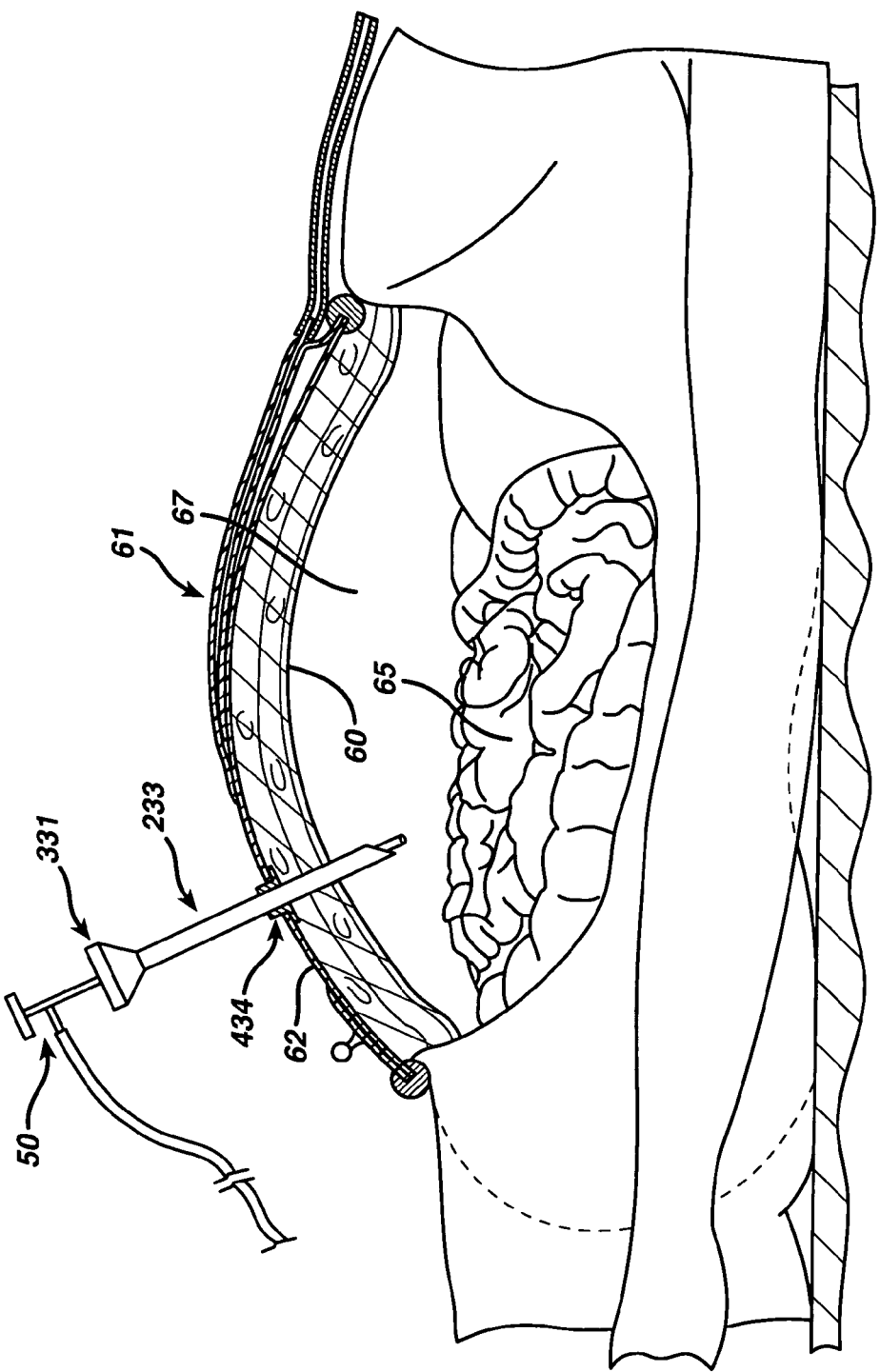
FIG. 26 is a perspective view illustrating the cap releasably attached to the cannula, and the cannula being used to provide access through the vacuum shell and the patient's body wall into the body cavity, and with a sleeve employed about the cannula to maintain an air seal between the cannula and the exterior of the patient's body such that operative space may be maintained.

The cannula extension 132 can be detached from the cannula 233, and cap 331 can be detached from cannula extension 132 and releasably attached to cannula 233. The reconfigured device 30 now comprises the cap 331 releasably joined to the proximal end of the cannula 233, as shown in FIG. 26. Cannula 233 provides a flow passage for ambient air pressure to body cavity 67. Additionally, various medical devices, such as endoscopic medical devices, can be introduced into body cavity 67 through the cap 331 and cannula 233.

The cannula 233 positioned as shown in FIG. 26 can provide a number of functions, including without limitation: providing bi-directional passage of air to maintain an ambient condition inside operative space the body cavity 67; venting of fumes and odors that may be generated due to cauterization of internal organs 65 to maintain good visibility inside the operative space; permitting multiple instrument exchange without loss of operative space; maintaining the incision open and thereby provide continuous access to the internal body cavity 67; permitting simultaneous passage of two or more instruments through the cannula 233; removal of tissue or body fluid from the operative through the cannula 233 (possible in part because a valve is not required as is needed in a typical cannula); and introducing medications or diagnostic probes through the cannula 233 either during the procedure or post operatively.

When the procedure is complete, the vacuum associated with the vacuum shell 61 can be released, so that body wall 60 drops to its original configuration. The cap 331 can be detached, and the shell 61 can be removed while keeping cannula 233 in place in the incision 59. The cannula 233 can be used to introduce a drainage catheter before final removal or closure of incision 59. Alternatively, it may be fitted with a new solid non-hollow cap similar to cap 331 but without the inner lumen 358 to provide an access conduit that is sealed from ambient conditions and which can then be used for visualization of the procedure site within the body cavity, such as for post operative inspection for any suspected bleeding or drainage until such time as the surgeon decides to close the incision.

While the present invention has been illustrated by description of several embodiments, it is not the intention of the applicant to restrict or limit the spirit and scope of the appended claims to such detail. Numerous other variations, changes, and substitutions will occur to those skilled in the art without departing from the scope of the invention. For instance, but without limitation, the multicomponent access device can be provided with a vacuum shell in kit form. Moreover, the structure of each element associated with the present invention can be alternatively described as a means for providing the function performed by the element. It will be understood that the foregoing description is provided by way of example, and that other modifications may occur to those skilled in the art without departing from the scope and spirit of the appended Claims.

The invention claimed is:

1. An assembly comprising:
  a vacuum device having a perimeter portion sized and shaped to be positioned against a portion of a patient's body and shell portion disposed inward of the perimeter portion, the shell portion having a generally convex outer surface and a generally concave inner surface, the vacuum device operable for providing an operative space within a patient; and
  a multicomponent device for providing access through the shell portion from a point external of the vacuum device to a point within the patient; the multicomponent device comprising detachable first and second members, the first member for providing a first portion of an access passageway, and the second member for providing a second portion of an access passageway, the first member comprising a proximal end, a pointed distal end, and an attachment portion positioned between the proximal and distal ends, the attachment portion comprising a means for attaching to a proximal end of the second member.

2. The assembly of claim 1 wherein the first member has an open distal tip at the distal end.

3. The assembly of claim 1 wherein the first member has a closed distal tip at the distal end.

4. The assembly of claim 1 wherein at the distal end has a pointed tip selected from the group consisting of bifurcated and non-bifurcated tips.

5. The assembly of claim 1 wherein the first member comprises a relatively rigid body portion and a relatively flexible distal end portion.

6. The assembly of claim 1 further comprising a cap releasably attachable to the proximal end of at least one of the first member and the second member.

7. The assembly of claim 1 further comprising a cap releasably attachable to the proximal end of both the first member and the second member.

8. The assembly of claim 1 wherein the first member comprises a tip at the distal end adapted to pierce a perforable membrane.

9. The assembly of claim 1 wherein the first member comprises at least one opening through a wall of the first member, the at least one opening spaced proximally of the distal end of the first member.

10. The assembly of claim 1 wherein the first member comprises a plurality of openings through the wall of the first member.

11. The assembly of claim 1 wherein the second member comprises a beveled distal end.

12. The assembly of claim 1 wherein the second member comprises at least one opening through a wall of the second member, the at least one opening spaced proximally of the distal end of the second member.

13. The assembly of claim 1 comprising a sleeve positionable along an outside surface of the first member.

14. The assembly of claim 1 wherein at least one of the first and second members comprises a generally transparent wall.

15. The assembly of claim 1 wherein at least one of the first and second members comprises a non-circular cross section.

* * * * *